(12) United States Patent
Jensen et al.

(10) Patent No.: US 7,199,233 B1
(45) Date of Patent: Apr. 3, 2007

(54) ARTIFICIAL PROMOTER LIBRARIES FOR SELECTED ORGANISMS AND PROMOTERS DERIVED FROM SUCH LIBRARIES

(76) Inventors: Peter Ruhdal Jensen, Soegaardsvcj 19, DK-2820 Gentofte (DK); Karin Hammer, Gaerdesmuttevej 20, DK-2970 Hoersholm (DK)

( * ) Notice: Subject to any disclaimer, the term of this patent is extended or adjusted under 35 U.S.C. 154(b) by 0 days.

(21) Appl. No.: 09/242,657

(22) PCT Filed: Aug. 25, 1997

(86) PCT No.: PCT/DK97/00342

§ 371 (c)(1),
(2), (4) Date: Feb. 19, 1999

(87) PCT Pub. No.: WO98/07846

PCT Pub. Date: Feb. 26, 1998

(30) Foreign Application Priority Data

Aug. 23, 1996  (DK) ..................................... 0886/96

(51) Int. Cl.
*C07H 21/04* (2006.01)
*C12Q 1/68* (2006.01)
(52) U.S. Cl. .......................................... 536/24.1; 435/6
(58) Field of Classification Search ............... 536/24.1, 536/23.1; 435/6, 320.1, 440
See application file for complete search history.

(56) References Cited

FOREIGN PATENT DOCUMENTS

WO         WO 942609 A1    11/1994

OTHER PUBLICATIONS

James E. Bailey, "Towards a Science of Metabolic Engineering", Science, vol. 252, pp. 1668-1675, 1991.*
Nucleic Acids Research, vol. 16, No. 15, 1988, Arnold R. Oliphant et al., "Defining the concensus sequences of *E. coli* promoter elements by random selection" p. 7673-p. 7683.
Dialog Information Services, file 155, MEDLINE, Dialog accession No. 08012585, Medline accession No. 94368841, Nilsson D et al.: "A conserved sequence in tRNA and rRNA promoters of *Lactococcus lactis*"; & Biochim Biophys Acta Sep. 13, 1994, 1219 (1) p. 141-4.
Marjolaine Crabeel, et al., Further Definition of the Sequence and Position Requirements of the Arginine Control Element that Mediates Repression and Induction by Arginine in *Saccharomyces cerevisiae*, Yeast vol. 11: 1367-1380 (1995).
W.M. DeVos and G.F.M. Simons, Gene cloning and expression systems in Lactococci, Genetics and Biotechnlogy of Lactic Acid Bacteria, pp. 52-105 (1994).
Michael J. Gasson, Plasmid Complements of *Streptococcus lactis* NCDO 712 and Other Lactic Streptococci After Protoplast-Induced Curing, Journal of Bacteriology, Apr. 1983, pp. 1-9.
Leonard Guarente, Yeast Promoters and *lacZ* Fusions Designed to Study Expression of Cloned Genes in Yeast, Methods in Enzymology, vol. 101, 1983, pp. 181-191.

Hannes Hermann, et al., pYLZ vectors: *Saccharomyces cerevisiae/Escherichia coli* shuttle plasmids to analyze yeast promoters, Gene. 119 (1992) 137-141.
Alan G. Hinnebusch, General and Pathway-specific Regulatory Mechanisms Controlling the Synthesis of Amino Acid Biosynthetic Enzymes in *Sacccharomyces cerevisiae*, vol. II, The Molecular and Cellular Biology of the Yeast Saccharomyces: *Gene Expression* (1992).
Helge Holo and Ingolf F. Nes, High-Frequency Transformation, by Electroporation, of *Lactococcus lactis* subsp. *cremoris* Grown with Glycine in Osmotically Stabilized Media, Applied and Envrionmemtal Microbiology, Dec. 1989, p. 3119-3123.
Hans Israelsen, et al., Cloning and Partial Characterization of Regulated Promoters from *Lactococcus lactis* Tn917-lacZ Integrants with the New Promoter Probe Vector, pAK80, Applied and Envrionmemtal Microbiology, Jul. 1995, p. 2540-2547.
Peter Ruhdal Jensen, et al., Excess capacity of $H^+$-ATPase and inverse respiratory control in *Escherichia coli*, The EMBO Journal, vol. 12, No. 4, pp. 1277-1282, 1993.
H. Kacser and J.A. Burns, The Control Of Flux, Symposia of the Society for Experimental Biology (1973) 17, 65-104.
Sambrook, Fritsch & Maniatis, Preparation and Transformation of Competent *E. coli*, Molecular Cloning, A Laboratory Manual, Second Edition (1982).

(Continued)

Primary Examiner—Daniel M. Sullivan
Assistant Examiner—Laura McGillem
(74) Attorney, Agent, or Firm—Hunton & Williams LLP

(57) ABSTRACT

An artificial promoter library (or a set of promoter sequences) for a selected organism or group of organisms is constructed as a mixture of double stranded DNA fragments, the sense strands of which comprise at least two consensus sequences of efficient promoters from said organism or group of organisms, or parts thereof comprising at least half of each, and surrounding intermediate nucleotide sequences (spacers) of variable length in which at least 7 nucleotides are selected randomly among the nucleobases A, T, C and G. The sense strands of the double stranded DNA fragments may also include a regulatory DNA sequence imparting a specific regulatory feature, such as activation by a change in the growth conditions, to the promoters of the library. Further, they may have a sequence comprising one or more recognition sites for restriction endonucleases added to one or both of their ends. The selected organism or group of organisms may be selected from prokaryotes and from eukaryotes; and in prokaryotes the consensus sequences to be retained most often will comprise the −35 signal (−35 to −30): TTGACA and the −10 signal (−12 to −7): TATAAT or parts of both comprising at least 3 conserved nucleotides of each, while in eukaryotes said consensus sequences should comprise a TATA box and at least one upstream activation sequence (UAS). Such artificial promoter libraries can be used, e.g., for optimizing the expression of specific genes in various selected organisms.

1 Claim, 5 Drawing Sheets

OTHER PUBLICATIONS

Jeffrey H. Miller, Experiments in Molecular Genetics, Society of Fellows, Harvard University and Départment de Biologie Moléculaire, Université de Genève, Cold Spring Harbor Laboratory (1972).

Dan Nilsson and Eric Johansen, A conserved sequence in tRNA and rRNA promoters of *Lactococcus lactis*, Biochimica et Biophysica Acta 1219 (1994) 141-144.

Stephen G. Oliver and John R. Warmington, Transcription, The Yeasts vol. 3, 2nd edition (1989).

Ine Schaaff, et al., Overproduction of Glycolytic Enzymes in Yeast, Yeast vol. 5: 285-290 (1989).

Martien Van Asseldonk, et al., Cloning, Nucleotide Sequence, and Regulatory Analysis of the *Lactococcus lactis dnaJ* Gene, Journal of Bacteriology, Mar. 1993, p. 1637-1644.

C. Casas et al., "*Sequence Analysis of a 9873 bp Fragment of the Left Arm of Yeast Chromosome XV that contains the ARG8 and CDC33 Genes, a Putative Riboflavin Synthase Beta Chain Gene and Four New Open Reading Frames*", YEAST vol. 11, pp. 1061-1067, (1995).

T. Eaton et al., "*Cloning and sequence analysis of the dnaK gene region of Lactococcus lactis subsp. lactis*", Journal of General Microbiology (1993), 139, pp. 3253-3264.

* cited by examiner

Artificial yeast promoters, regulation by external arginine

Artificial yeast promoters, general regulation by external amino acids

US 7,199,233 B1

SEQUENCE LISTING

```
<160> NUMBER OF SEQ ID NOS: 62

<210> SEQ ID NO 1
<211> LENGTH: 100
<212> TYPE: DNA
<213> ORGANISM: Lactococcus lactis
<220> FEATURE:
<221> NAME/KEY: modified_base
<222> LOCATION: (26)..(30)
<223> OTHER INFORMATION: "n" may be a, t, c, g, other or unknown
<220> FEATURE:
<221> NAME/KEY: modified_base
<222> LOCATION: (46)..(59)
<223> OTHER INFORMATION: "n" may be a, t, c, g, other or unknown
<220> FEATURE:
<221> NAME/KEY: modified_base
<222> LOCATION: (70)..(71)
<223> OTHER INFORMATION: "n" may be a, t, c, g, other or unknown
<220> FEATURE:
<221> NAME/KEY: modified_base
<222> LOCATION: (73)
<223> OTHER INFORMATION: "n" may be a, t, c, g, other or unknown

<400> SEQUENCE: 1
cgggatcctt aagaatatta tgcatnnnnn agtttattct tgacannnnn nnnnnnnnnt    60
ggtataatan nanagtactg ttaactgcag ctgaattcgg                         100
```

<210> SEQ ID NO 2
<211> LENGTH: 113
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: modified_base
<222> LOCATION: (32)..(40)
<223> OTHER INFORMATION: "n" may be a, t, c, g, other or unknown
<220> FEATURE:
<221> NAME/KEY: modified_base
<222> LOCATION: (61)..(74)
<223> OTHER INFORMATION: "n" may be a, t, c, g, other or unknown
<220> FEATURE:
<221> NAME/KEY: modified_base
<222> LOCATION: (85)..(86)
<223> OTHER INFORMATION: "n" may be a, t, c, g, other or unknown
<220> FEATURE:
<221> NAME/KEY: modified_base
<222> LOCATION: (88)
<223> OTHER INFORMATION: "n" may be a, t, c, g, other or unknown

<400> SEQUENCE: 2
cgggatccaa gcttaatatt aattagcact cnnnnnnnnn gagtgctaat tttttgaca      60 nnnnnnnnnn nnntggtat aatannanag tactgcagct gtctagaatt cgg           113

<210> SEQ ID NO 3
<211> LENGTH: 199
<212> TYPE: DNA
<213> ORGANISM: Saccharomyces cerevisiae
<220> FEATURE:
<221> NAME/KEY: modified_base
<222> LOCATION: (17)..(76)
<223> OTHER INFORMATION: "n" may be a, t, c, g, other or unknown
<220> FEATURE:
<221> NAME/KEY: modified_base
<222> LOCATION: (83)..(121)
<223> OTHER INFORMATION: "n" may be a, t, c, g, other or unknown

<400> SEQUENCE: 3
cagaattcgt gactcannnn nnnnnnnnn nnnnnnnnn nnnnnnnnn nnnnnnnnn         60 nnnnnnnnnn nnnnntata aannnnnnnn nnnnnnnnn nnnnnnnnn nnnnnnnnn        120 nctcttaagt gcaagtgact gcgaacattt ttttcgtttg ttagaataat tcaagaatcg    180
ctaccaatca tggatcccg                                                 199

<210> SEQ ID NO 4
<211> LENGTH: 45
<212> TYPE: DNA
<213> ORGANISM: Pseudomonas putida
<220> FEATURE:
<221> NAME/KEY: modified_base
<222> LOCATION: (1)..(8)
<223> OTHER INFORMATION: "n" may be a, t, c, g, other or unknown
<220> FEATURE:
<221> NAME/KEY: modified_base
<222> LOCATION: (13)..(31)
<223> OTHER INFORMATION: "n" may be a, t, c, g, other or unknown
<220> FEATURE:
<221> NAME/KEY: modified_base
<222> LOCATION: (38)..(45)
<223> OTHER INFORMATION: "n" may be a, t, c, g, other or unknown

<400> SEQUENCE: 4
nnnnnnnntt grnnnnnnnn nnnnnnnnnn ntatratnnn nnnnn                     45

```
<210> SEQ ID NO 5
<211> LENGTH: 60
<212> TYPE: DNA
<213> ORGANISM: Lactococcus lactis

<400> SEQUENCE: 5
cataccggag tttattcttg acagttccac ctcgggttga tataatatct cagtactgtt      60

<210> SEQ ID NO 6
<211> LENGTH: 60
<212> TYPE: DNA
<213> ORGANISM: Lactococcus lactis

<400> SEQUENCE: 6
catggcttag tttattcttg acagggtagt atcactgtga tataatagga cagtactgtt      60

<210> SEQ ID NO 7
<211> LENGTH: 59
<212> TYPE: DNA
<213> ORGANISM: Lactococcus lactis

<400> SEQUENCE: 7
cataagtgag tttattcttg acccggacgc cccccttga tataataagt agtactgtt        59

<210> SEQ ID NO 8
<211> LENGTH: 60
<212> TYPE: DNA
<213> ORGANISM: Lactococcus lactis

<400> SEQUENCE: 8
catatacaag tttattcttg acactagtcg gccaaaatga tataatacct gagtactgtt     60

<210> SEQ ID NO 9
<211> LENGTH: 60
<212> TYPE: DNA
<213> ORGANISM: Lactococcus lactis

<400> SEQUENCE: 9
catgctttac tttattcttg acaaaaccac cagcttttgg tataatacgt gagaactgtt     60

<210> SEQ ID NO 10
<211> LENGTH: 60
<212> TYPE: DNA
<213> ORGANISM: Lactococcus lactis

<400> SEQUENCE: 10
catgacggag tttattcttg acacaggtat ggacttatga tataataaaa cagtactgtt     60

<210> SEQ ID NO 11
<211> LENGTH: 60
<212> TYPE: DNA
<213> ORGANISM: Lactococcus lactis
<220> FEATURE:
<221> NAME/KEY: modified_base
<222> LOCATION: (7)
<223> OTHER INFORMATION: "n" may be a, t, c, g, other or unknown
<220> FEATURE:
<221> NAME/KEY: modified_base
<222> LOCATION: (13)
<223> OTHER INFORMATION: "n" may be a, t, c, g, other or unknown

<400> SEQUENCE: 11
cattacntag ttnattcttg acagaattac gattcgctgg tataatatat cagtactgtt     60

<210> SEQ ID NO 12
```

```
<211> LENGTH: 58
<212> TYPE: DNA
<213> ORGANISM: Lactococcus lactis

<400> SEQUENCE: 12
cattgtgtag tttattcttg acagctatga gtcaatttgg tataataaca gtactcag      58

<210> SEQ ID NO 13
<211> LENGTH: 59
<212> TYPE: DNA
<213> ORGANISM: Lactococcus lactis

<400> SEQUENCE: 13
cattctggag tttattcttg accgctcagt atgcagtggt ataatagtac agtactgtt     59

<210> SEQ ID NO 14
<211> LENGTH: 58
<212> TYPE: DNA
<213> ORGANISM: Lactococcus lactis

<400> SEQUENCE: 14
cattttgcag tttattcttg acattgtgtg cttcgggtgt ataatactaa gtactgtt      58

<210> SEQ ID NO 15
<211> LENGTH: 58
<212> TYPE: DNA
<213> ORGANISM: Lactococcus lactis

<400> SEQUENCE: 15
catcgcttag tttttcttga caggagggat ccgggttgat ataatagtta gtactgtt      58

<210> SEQ ID NO 16
<211> LENGTH: 60
<212> TYPE: DNA
<213> ORGANISM: Lactococcus lactis

<400> SEQUENCE: 16
catttgctag tttattcttg acatgaagcg tgcctaatgg tatattactt gagtactgtt    60

<210> SEQ ID NO 17
<211> LENGTH: 60
<212> TYPE: DNA
<213> ORGANISM: Lactococcus lactis
<220> FEATURE:
<221> NAME/KEY: modified_base
<222> LOCATION: (32)
<223> OTHER INFORMATION: "n" may be a, t, c, g, other or unknown

<400> SEQUENCE: 17
catgggtgag tttattcttg acagtgcggc cngggctga tatcatagca gagtactatt     60

<210> SEQ ID NO 18
<211> LENGTH: 59
<212> TYPE: DNA
<213> ORGANISM: Lactococcus lactis

<400> SEQUENCE: 18
cattaccgag tttattcttg acaccgttta tcggggttgt ataatactat agtactgtt    59

<210> SEQ ID NO 19
<211> LENGTH: 60
<212> TYPE: DNA
<213> ORGANISM: Lactococcus lactis

<400> SEQUENCE: 19
```

```
catgtaggag tttattcttg acagattagt taggggggtgg tataatatct cagtactgtt    60
```

<210> SEQ ID NO 20
<211> LENGTH: 60
<212> TYPE: DNA
<213> ORGANISM: Lactococcus lactis

<400> SEQUENCE: 20

```
catgggtaag tttattcttc acactatctg ggcccgatgg tataataagt gactactgtt    60
```

<210> SEQ ID NO 21
<211> LENGTH: 59
<212> TYPE: DNA
<213> ORGANISM: Lactococcus lactis

<400> SEQUENCE: 21

```
ctttggcagt tttattcttga catgtagtga gggggctggt ataatcacat agtactgtt    59
```

<210> SEQ ID NO 22
<211> LENGTH: 60
<212> TYPE: DNA
<213> ORGANISM: Lactococcus lactis

<400> SEQUENCE: 22

```
cattctacag tttattcttg acattgcact gtcccctgg tataataact atacatgcat     60
```

<210> SEQ ID NO 23
<211> LENGTH: 60
<212> TYPE: DNA
<213> ORGANISM: Lactococcus lactis

<400> SEQUENCE: 23

```
catggggccg tttattcttg acaacggcga gcagacctgg tataataata tagtactgtt    60
```

<210> SEQ ID NO 24
<211> LENGTH: 59
<212> TYPE: DNA
<213> ORGANISM: Lactococcus lactis

<400> SEQUENCE: 24

```
catcggtaag tttattcttga catctcaggg gggacgtggt ataataactg agtactgtt    59
```

<210> SEQ ID NO 25
<211> LENGTH: 60
<212> TYPE: DNA
<213> ORGANISM: Lactococcus lactis
<220> FEATURE:
<221> NAME/KEY: modified_base
<222> LOCATION: (29)..(30)
<223> OTHER INFORMATION: "n" may be a, t, c, g, other or unknown

<400> SEQUENCE: 25

```
catcctgtag tttattcttg acacacgtnn ttagctgtgg tataatagga gagtactgtt    60
```

<210> SEQ ID NO 26
<211> LENGTH: 60
<212> TYPE: DNA
<213> ORGANISM: Lactococcus lactis

<400> SEQUENCE: 26

```
catgacagag tttattcttg acagtattgg gttactttgg tataatagtt gagtactgtt    60
```

<210> SEQ ID NO 27

-continued

<210> SEQ ID NO 27
<211> LENGTH: 60
<212> TYPE: DNA
<213> ORGANISM: Lactococcus lactis

<400> SEQUENCE: 27
catacgggag tttattcttg acatattgcc ggtgtgttgg tataataact tagtactgtt    60

<210> SEQ ID NO 28
<211> LENGTH: 60
<212> TYPE: DNA
<213> ORGANISM: Lactococcus lactis

<400> SEQUENCE: 28
catgttggag tttattcttg acatacaatt actgcagtga tataataggt gagtactgtt    60

<210> SEQ ID NO 29
<211> LENGTH: 60
<212> TYPE: DNA
<213> ORGANISM: Lactococcus lactis

<400> SEQUENCE: 29
catcgcgaag tttattcttc acacaccgca gaacttgtgg tataatacaa cagtactgtt    60

<210> SEQ ID NO 30
<211> LENGTH: 59
<212> TYPE: DNA
<213> ORGANISM: Lactococcus lactis

<400> SEQUENCE: 30
catcattaag tttattcttc acattggccg gaattgttgt ataatacctt agtactgtt     59

<210> SEQ ID NO 31
<211> LENGTH: 60
<212> TYPE: DNA
<213> ORGANISM: Lactococcus lactis

<400> SEQUENCE: 31
catagagaag tttattcttg acagctaact tggcctttga tataatacat gagtactgtt    60

<210> SEQ ID NO 32
<211> LENGTH: 60
<212> TYPE: DNA
<213> ORGANISM: Lactococcus lactis

<400> SEQUENCE: 32
cattgcgaag tttattcttg acagtacgtt tttaccatga tataatagta tagtactgtt    60

<210> SEQ ID NO 33
<211> LENGTH: 60
<212> TYPE: DNA
<213> ORGANISM: Lactococcus lactis

<400> SEQUENCE: 33
gatgttttag tttattcttg acaccgtatc gtgcgcgtga tataatcggg atccttaaga    60

<210> SEQ ID NO 34
<211> LENGTH: 59
<212> TYPE: DNA
<213> ORGANISM: Lactococcus lactis

<400> SEQUENCE: 34
catagaacag tttattcttg acattgaata agaaggctga tataatagcc agtactgtt     59

```
<210> SEQ ID NO 35
<211> LENGTH: 60
<212> TYPE: DNA
<213> ORGANISM: Lactococcus lactis

<400> SEQUENCE: 35
catccgcaag tttattcttg acagctgaat gtagacgtgg tataatagtt aagtactgtt      60

<210> SEQ ID NO 36
<211> LENGTH: 60
<212> TYPE: DNA
<213> ORGANISM: Lactococcus lactis

<400> SEQUENCE: 36
cattcgtaag tttattcttg acacctgaga tgaggcgtga tataataaat aagtactgtt      60

<210> SEQ ID NO 37
<211> LENGTH: 59
<212> TYPE: DNA
<213> ORGANISM: Lactococcus lactis

<400> SEQUENCE: 37
catcgggtag tttattcttg acaattaagt agagcctgat ataatagttc agtactgtt       59

<210> SEQ ID NO 38
<211> LENGTH: 59
<212> TYPE: DNA
<213> ORGANISM: Lactococcus lactis

<400> SEQUENCE: 38 catggggag tttattcttg acatcatctt cgtagcctgg tatactacat gagtatgtt        59

<210> SEQ ID NO 39
<211> LENGTH: 60
<212> TYPE: DNA
<213> ORGANISM: Lactococcus lactis

<400> SEQUENCE: 39
catgtgggag tttattcttg acacagatat ttccggatga tataataact gagtactgtt      60

<210> SEQ ID NO 40
<211> LENGTH: 60
<212> TYPE: DNA
<213> ORGANISM: Lactococcus lactis

<400> SEQUENCE: 40
tatgcggtag tttattcttg acatgacgag acaggtgtgg tataatgggt ctagattagg      60

<210> SEQ ID NO 41
<211> LENGTH: 60
<212> TYPE: DNA
<213> ORGANISM: Lactococcus lactis

<400> SEQUENCE: 41
cattctttag tttattcttg acaaacgtat tgaggactga tataataggt gagtactgtt      60

<210> SEQ ID NO 42
<211> LENGTH: 60
<212> TYPE: DNA
<213> ORGANISM: Lactococcus lactis

<400> SEQUENCE: 42
catagtctag tttattcttg acacgcggtc cattggctgg tataataatt tagtactgtt      60
```

<210> SEQ ID NO 43
<211> LENGTH: 177
<212> TYPE: DNA
<213> ORGANISM: Saccharomyces cerevisiae

<400> SEQUENCE: 43
gaattcgtga ctcaaacggg tggtcgacgg gtggttccaa ttaattggcg tccctcttat      60
aaaggcgagg gtacgtgcga caattggtag agcgagcggg gctcttaagt gcaagtgact     120
gcgaacattt ttttcgtttg ttagaataat tcaagaatcg ctaccaatca tggatcc        177

<210> SEQ ID NO 44
<211> LENGTH: 182
<212> TYPE: DNA
<213> ORGANISM: Saccharomyces cerevisiae

<400> SEQUENCE: 44
gaattcgtga ctcacggcat ctgatggttg accatagtca ggaacattgt gctggagttc      60
cttgaggaat gagttataaa atgggaggtt gcggctaatg ccaggcagga gaggaaccct     120
cttaagtgca agtgactgca acatttttt tcgtttgttg aatcgctacc aatcatggat     180
cc                                                                   182

<210> SEQ ID NO 45
<211> LENGTH: 191
<212> TYPE: DNA
<213> ORGANISM: Saccharomyces cerevisiae

<400> SEQUENCE: 45
gaattcgtga ctcactaggc aggtcacgtt ggctcttcgc ggcgcaggtt cgtatgccgc      60
gccgccaggg gctttataaa ggtcgtcctg gtacagttgg gatggctcc acgtttcggc     120 tcttaagtgc aagtgactgc gaacatttcg tttgttagaa taattcaaga atcgctacca     180
atcatggatc c                                                         191

<210> SEQ ID NO 46
<211> LENGTH: 167
<212> TYPE: DNA
<213> ORGANISM: Saccharomyces cerevisiae

<400> SEQUENCE: 46
gaattcgtga ctcagggccg tactaagtag ctttcgtatg ctatgcgggg ttttataaat      60
ctttgggcca tggtcttgct ggaaaacacc tctcttaagt gcaagtgact gcgaacattt     120
ttttcgtttg ttagaataat tcaagaatcg ctaccaatca tggatcc                  167

<210> SEQ ID NO 47
<211> LENGTH: 191
<212> TYPE: DNA
<213> ORGANISM: Saccharomyces cerevisiae

<400> SEQUENCE: 47
gaattcgtga ctcaccgctc gggtgcaggg ccaaggcggc ggaatgtgcg gggcgttcta      60
gcgcaatcgg ggtataaatt tataaggagg ctgcgggtgc tagtttgtct agtttgactc     120
ttaagtgcaa gtgactgcga acatttttcg tttgttagaa taattcaaga atcgctacca     180
atcatggatc c                                                         191

<210> SEQ ID NO 48
<211> LENGTH: 195

<212> TYPE: DNA
<213> ORGANISM: Saccharomyces cerevisiae

<400> SEQUENCE: 48

```
gaattcgtga ctcaggatta gctatgccgg ttgggataag cgaacaactg gaggtgagaa    60
gctttttgtc agaatataaa cccgttagtc agggtttggt gggatagggg gtactgtacc   120
tcttaagtgc aagtgactgc gaacattttt ttcgtttgtt agaataattc aagaatcgct   180
accaatcatg gatcc                                                    195
```

<210> SEQ ID NO 49
<211> LENGTH: 179
<212> TYPE: DNA
<213> ORGANISM: Saccharomyces cerevisiae

<400> SEQUENCE: 49

```
gaattcgtga ctcactaagg gttcgccatt aacagaatcg ctggtagaac atcggtagtt    60
aggcacccga gtataaacag gcggacccct cacggatatc agctgatagt gcgagcctca   120
atgcgaacat tttttcgtt tgttagaata attcaagaat cgctaccaat catggatcc    179
```

<210> SEQ ID NO 50
<211> LENGTH: 195
<212> TYPE: DNA
<213> ORGANISM: Saccharomyces cerevisiae

<400> SEQUENCE: 50

```
gaattcgtga ctcagtatcc acgggtgttt gagggctggt cgcaggttag caggcgaggg    60
cgggtggtta cggctataaa tgagtgtttg cagccgggta cgggcgtacg agtagtgatc   120
tcttaaatgc aagtgactgc gaacattttt ttcgtttgtt agaataattc aagaatcgct   180
accaatcatg gatcc                                                    195
```

<210> SEQ ID NO 51
<211> LENGTH: 193
<212> TYPE: DNA
<213> ORGANISM: Saccharomyces cerevisiae

<400> SEQUENCE: 51

```
gaattcgtga ctcaatgctg cgggcggcag gagtctggtg taacttccca ttttgagtga    60
agacagacc atctataaac atttggtggg caaagtggcc tggcggattt gtttggactc    120
ttaagtgaaa gtgactgcga acattttttt cgtttgttag aataattcaa gaatcgctac   180
caatcatgga tcc                                                      193
```

<210> SEQ ID NO 52
<211> LENGTH: 166
<212> TYPE: DNA
<213> ORGANISM: Saccharomyces cerevisiae

<400> SEQUENCE: 52

```
gaattcgtga ctcacttaag gctactgcgg aagtttagat ctaaggtcgg aaataattta    60
gaaaattacg acattataaa tagcggagag gccaggtgat gggcaccatt gtggggggc    120
tcttaattgt tagaataatt caagaatcgc taccaatcat ggatcc                  166
```

<210> SEQ ID NO 53
<211> LENGTH: 195
<212> TYPE: DNA
<213> ORGANISM: Saccharomyces cerevisiae

```
<400> SEQUENCE: 53
gaattcgtga ctcagtcgcc cgcaagatgg gatggtgcat tttaaacacc cgaattatac      60
tcgtcaactt atagtataaa cggaacgcga cgatacgttc tagttttcgg cgaagtcgac     120
tcttaagtgc aagtgactgc gaacattttt ttcgtttgtt agaataattc aagaatcgct     180
accaatcatg gatcc                                                      195

<210> SEQ ID NO 54
<211> LENGTH: 188
<212> TYPE: DNA
<213> ORGANISM: Saccharomyces cerevisiae

<400> SEQUENCE: 54
gaattcgtac tcacgacagc gttatgactt cgaggaccag ctacttccgg tcgcgtacta      60
gtttttacct gtataaactt tgctaccgct gggccttggt ggtgctgtcc cgctcttaag     120
tgcaagtgac tgcgaacatt ttttttcgttt gttacaataa ttcaagaatc gctaccaatc    180
atggatcc                                                              188

<210> SEQ ID NO 55
<211> LENGTH: 195
<212> TYPE: DNA
<213> ORGANISM: Saccharomyces cerevisiae

<400> SEQUENCE: 55
gaattcgtga ctaaatggat aaggttatcg ccatcacgga gtcttctctc acgtctggag      60
cagaggctag accttataaa ttatacatgg tgggagaggc gatagtcttt agagacgtgc     120
tcttaagtgc aagtgactgc gaacattttt ttcgtttgtt agaataattc aagaatcgct     180
accaatcatg gatcc                                                      195

<210> SEQ ID NO 56
<211> LENGTH: 189
<212> TYPE: DNA
<213> ORGANISM: Saccharomyces cerevisiae

<400> SEQUENCE: 56
gaattcgtga ctcacaagaa tgtgggcggg tcgttaaact gagcctggac accttggctg      60
cgtcgctttc gtataaagat cttagagctg tggagtctgg gtcgagtggc cagctcttaa     120
atgcaagtga ctgcgaacat tttttcgtt tgttagaata attcaagaat cgctaccaat     180
catggatcc                                                             189

<210> SEQ ID NO 57
<211> LENGTH: 195
<212> TYPE: DNA
<213> ORGANISM: Saccharomyces cerevisiae

<400> SEQUENCE: 57
gaattcgtga ctcactcgga agattgggtt tacgattagg atggcgcggc agaaccgggg      60
gggattccct tctatataaa gggttccgat actacgtgct gcggacggcc gatcgagtta     120
tcttaagtgc aagtgactgc gaaaattttt ttcgtttgtt agaataattc aagaatcgct     180
accaatcatg gatcc                                                      195

<210> SEQ ID NO 58
<211> LENGTH: 176
<212> TYPE: DNA
<213> ORGANISM: Saccharomyces cerevisiae
```

```
<400> SEQUENCE: 58
gaattcgtga ctcatctagt gagaggagcc gtggtatctt gtgtcaccac caggggaaaa      60
taatggcagg ggtgtataaa tggtcgagta gtcgcgaccc acgctgcaag gcaaggaact    120
cttaaatttt tttcgtttgt tagaataatt caagaatcgc taccaatcat ggatcc        176

<210> SEQ ID NO 59
<211> LENGTH: 23
<212> TYPE: DNA
<213> ORGANISM: Saccharomyces cerevisiae

<400> SEQUENCE: 59
ctcttaagtg caagtgactg cga                                              23

<210> SEQ ID NO 60
<211> LENGTH: 52
<212> TYPE: DNA
<213> ORGANISM: Lactococcus lactis
<220> FEATURE:
<221> NAME/KEY: modified_base
<222> LOCATION: (16)..(29)
<223> OTHER INFORMATION: "n" may be a, t, c, g, other or unknown
<220> FEATURE:
<221> NAME/KEY: modified_base
<222> LOCATION: (40)..(41)
<223> OTHER INFORMATION: "n" may be a, t, c, g, other or unknown
<220> FEATURE:
<221> NAME/KEY: modified_base
<222> LOCATION: (43)
<223> OTHER INFORMATION: "n" may be a, t, c, g, other or unknown

<400> SEQUENCE: 60
agtttattct tgacannnnn nnnnnnnnnt grtataatan nwnagtactg tt              52

<210> SEQ ID NO 61
<211> LENGTH: 27
<212> TYPE: DNA
<213> ORGANISM: Lactococcus lactis
<220> FEATURE:
<221> NAME/KEY: modified_base
<222> LOCATION: (10)..(18)
<223> OTHER INFORMATION: "n" may be a, t, c, g, other or unknown

<400> SEQUENCE: 61
ttagcactcn nnnnnnnnga gtgctaa                                          27

<210> SEQ ID NO 62
<211> LENGTH: 73
<212> TYPE: DNA
<213> ORGANISM: Lactococcus lactis
<220> FEATURE:
<221> NAME/KEY: modified_base
<222> LOCATION: (10)..(18)
<223> OTHER INFORMATION: "n" may be a, t, c, g, other or unknown
<220> FEATURE:
<221> NAME/KEY: modified_base
<222> LOCATION: (39)..(52)
<223> OTHER INFORMATION: "n" may be a, t, c, g, other or unknown
<220> FEATURE:
<221> NAME/KEY: modified_base
<222> LOCATION: (63)..(64)
<223> OTHER INFORMATION: "n" may be a, t, c, g, other or unknown
<220> FEATURE:
<221> NAME/KEY: modified_base
<222> LOCATION: (66)
<223> OTHER INFORMATION: "n" may be a, t, c, g, other or unknown

<400> SEQUENCE: 62
```

```
ttagcactcn nnnnnnnnga gtgctaattt ttttgacann nnnnnnnnnn nntgrtataa    60
tannwnagta ctg                                                      73
```

ARTIFICIAL PROMOTER LIBRARIES FOR SELECTED ORGANISMS AND PROMOTERS DERIVED FROM SUCH LIBRARIES

FIELD OF THE INVENTION

This invention concerns artificial promoter libraries and a method of constructing an artificial promoter library for a selected organism or group of organisms. The invention also concerns the individual novel promoters derived from such libraries. Further, the invention concerns a method of optimizing the expression of a gene in a selected organism by use of promoters from such an artificial promoter library for that organism. In principle, artificial promoter libraries according to the invention can be constructed for use in any living organism, but presently they have mostly been of value for modulating gene expression of microorganisms. In connection with this invention the term "microorganism" shall be taken broadly to include prokaryotic organisms such as bacteria as well as eukaryotic microorganisms such as yeasts, other fungi and cell lines of higher organisms.

BACKGROUND OF THE INVENTION

Metabolic engineering of living organisms is still in its infancy with respect to industrial applications, despite the fact that genetic engineering has now been feasible for more than a decade. To a large extent, this may be due to the disappointing outcome of many of the attempts so far to improve strain performance. There are at least two reasons for the negative outcome of the attempts to increase metabolic fluxes:

One is that the genetic engineer tends to overlook the subtlety of control and regulation of cellular metabolism. The expression of enzymes that are expected to be rate limiting are increased 10 to 100 fold, e.g. by placing the gene on a high copy number plasmid. Or, a branching flux in a pathway is eliminated by deleting a gene. Quite often, this will have secondary effects on the metabolism, for instance by lowering metabolite concentrations that are essential to other parts of the cellular metabolism (e.g. processes that are essential to the growth of the organism) and the net result may be that the overall performance of the cell with respect to the desired product is decreased. Instead, it is necessary to tune the expression of the relevant gene around the normal expression level and determine the optimal expression level, for instance as the level that maximizes or minimizes the flux.

The second reason for the negative outcome lies in the rate limiting concept itself: both metabolic control theory (Kacser and Burns, 1973) and experimental determinations of control by individual steps in a pathway (Schaaff et al., 1989; Jensen et al., 1993) have shown that reaction steps which were expected to be rate limiting with respect to a particular flux, turned out to have no or very little control over the flux. Instead, the control and regulation of the cellular metabolism turned out to be distributed over several enzymes in a pathway, and it may be necessary to enhance the expression of several enzymes in order to obtain a higher flux.

According to metabolic control theory, the total flux control exerted by all the enzymes in a pathway, should always sum up to 1. Therefore, after one enzyme concentration has been optimized, the flux control will have shifted to another enzyme(s), and it may then be useful to perform additional rounds of enzyme optimization in order to increase the flux further.

In summary, flux optimization requires 1) fine-tuning of enzyme concentration rather than many fold overexpression and often 2) optimization of the level of several enzymes in a pathway rather than looking for the rate limiting step.

There are now many systems available that allow one to increase the gene expression more than 1000 fold and/or to turn on gene expression at a particular time point during a fermentation process (e.g. using temperature inducible systems). With respect to tuning the steady state gene expression in the fermenter, to say 150% or 70% of the normal expression level, it becomes more difficult. In principle, one could use a lac-type promoter in front of the gene of interest, and then add a certain amount of an inducer of the lac system, for instance IPTG (isopropyl-β-D-thiogalactoside), or use a temperature sensitive system at the correct temperature. These possibilities are often not practical for large scale industrial applications. The alternative is to use a promoter that has exactly the right strength. However, such promoters are seldom available, and furthermore one needs a range of promoter activities in order to optimize the expression of the gene in the first place, see below.

During the past two decades, much work has been done to define and optimize the consensus sequences of microorganisms. In many prokaryotes, one often finds two more or less conserved DNA sequences at approximately position –10 and –35 relative to the start site for transcription, TATAAT and TTGACA, respectively, with aproximately 17 basepairs between the two. The dogma in this field is that, by including these elements, the resulting promoters would tend to become strong. Indeed, promoter up mutations, which are relatively rare events, usually results in a better match to the above consensus sequences, while down mutations results in a poorer match to the consensus sequences or a less optimal distances between these. In addition, when random DNA sequences are cloned in place of one of the two consensus sequences, the strength of the resulting promoters usually correlate with the degree of homology to the consensus sequences.

In principle, modulation of the strength of promoters could then be achieved by basepair changes in the consensus sequences or by changes in the length of the spacer between these. But the impact of such changes on the promoter strength will tend to be large (see example 1 of this invention), and it is therefore not feasible to achieve small steps of strength modulation through base pair changes in the consensus sequences.

While the length of the spacer separating the two consensus sequences is known to play an important role for the strength of a promoter, the sequence of the spacers between the consensus sequences has usually been considered to be of little importance for the strength of the promoters, and attempts to identify additional consensus sequences in the spacer region through mutagenesis have indeed been unsuccessful. So far, nobody has attempted to randomize the spacer, while keeping the consensus sequences and the spacer length relatively constant.

Numerous experiments have been carried out in order to define and optimize the consensus sequences of microorganisms, including experiments where at least one of the consensus sequences was being randomized. In some of these experiments a part of the nucleotides surrounding the consensus sequences was also randomized in order to allow for the generation of promoters with length of spacers different from 17 bp, and/or in order to find possible new consensus motifs around the consensus sequences. The chances that this will generate an efficient promoter is very small and a selection must be applied in order to find those rare cases where the homology to the consensus sequence is sufficiently high to result in even a weak promoter.

OBJECT OF THE INVENTION

The promoter libraries that we are aiming at should cover the entire range of promoter activities that could become of interest for engineering of a particular species, preferably from the weakest promoters detectable, to the strongest promoters possible. Moreover, we aim at covering this broad activity range in small steps, say increase in activity by 50–100% per step in order to be suitable for the purpose of flux optimization as described above.

In this invention, we show that the sequence of the spacers between the consensus sequences are far more important than it has previously been appreciated. The spacer sequence can have a strong impact on promoter strength, when 1) a major part of the spacer sequence is varied simultaneously and in a random manner and 2), at the same time, at least half of the consensus sequences are kept constant. We show that if these two conditions are fulfilled, our method can be used to generate promoters that cover wide ranges of activities, including very strong promoters. The range of promoter activities is covered in small steps of activity change which makes these promoters very suitable for metabolic engineering purposes. In addition, we show that the method can be used to generate promoters for a wide range of organisms and at an unusual high frequency.

SUMMARY OF THE INVENTION

The present invention provides an artificial promoter library for a selected organism or group of organisms, comprising a mixture of double stranded DNA fragments the sense strands of which comprise at least two consensus sequences of efficient promoters from said organism or group of organisms, or parts thereof comprising at least half of each, and surrounding or intermediate nucleotide sequences (spacers) of variable length in which at least 7 nucleotides are selected randomly among the nucleobases A, T, C and G, with the proviso that previously known promoter sequences and promoter sequences isolated from natural sources are not comprised.

The broadest variation in promoter strengths is obtained when at least 10, preferably at least 12, and more preferably at least 14, nucleotides in the spacer sequence(s) are selected randomly among the nucleobases A, T, C and G.

The sense strands of the double stranded DNA fragments may also include a regulatory DNA sequence imparting a specific regulatory feature to the promoters of the library. Such specific regulatory feature is preferably activation by a change in the growth conditions, such as a change in the pH, osmolarity, temperature or growth phase.

For cloning purposes the double stranded DNA fragments usually have sequences comprising one or more recognition sites for restriction endonucleases added to one of or both their ends; most conveniently sequences specifying multiple recognition sites for restriction endonucleases (multiple cloning sites MCS).

The selected organism or group of organisms may be selected from prokaryotes and from eukaryotes, in particular from prokaryotes and eukaryotic microorganisms such as yeasts, other fungi and cell lines of higher organisms.

An interesting group of prokaryotes i.a. in the dairy industry consists of lactic acid bacteria of the genera *Lactococcus, Streptococcus, Enterococcus, Lactobacillus* and *Leuconostoc*, in particular strains of the species *Lactococcus lactis* and *Streptococcus thermophilus*. Other interesting prokaryotes are bacteria belonging to the genera *Escherichia, Bacillus* and *Pseudomonas*, in particular the species *Escherichia coli, Bacillus subtilis* and *Pseudomonas putida*.

In an artificial promoter library for prokaryotes said consensus sequences may for example comprise the −10 signal (−12 to −7): TATAAT and at least one activator protein binding site upstream of the −10 signal or parts thereof comprising at least 3 conserved nucleotides of each.

Most often the consensus sequences to be retained in an artificial promoter library for prokaryotes will comprise the −35 signal (−35 to −30): TTGACA and the −10 signal (−12 to −7): TATAAT or parts of both comprising at least 3 conserved nucleotides of each.

More efficient promoters are usually obtained when said consensus sequences comprise from 4 to 6 conserved nucleotides of the −35 signal and from 4 to 6 conserved nucleotides of the −10 signal, preferably 5 or 6, and more preferably all 6 nucleotides of each. The most efficient promoters are obtained when said consensus sequences further comprise intervening conserved motifs, e.g. selected from the conserved motifs −44 to −41: AGTT, −40 to −36: TATTC, −15 to −14: TG, and +1 to +8: GTACTGTT.

In such promoters the length of the spacer between the −35 signal and the −10 signal should be 14–23 bp, preferably 16–18 bp, and more preferably 17 bp. This should be understood to mean the spacer length between the hexamer signals, even when some of the nucleotides in the signals have been mutated.

In eukaryotic organisms said consensus sequences should comprise a TATA box and at least one upstream activation sequence (UAS).

An interesting eukaryotic microorganism is the yeast species *Saccharomyces cerevisiae*, normal baker's yeast. In promoters to be used in *Saccharomyces* the consensus sequences may further comprise a transcription initiation signal (TI box) functioning in *Saccharomyces cerevisiae*.

In a specific embodiment of an artificial promoter library according to the invention for *Saccharomyces cerevisiae* said consensus sequences comprise the TATA box: TATAAA, the $UAS_{GCN4_p}$: TGACTCA, and the TI box (SEQ ID NO:59): CTCTTAAGTGCAAGTGACTGCGA, which also functions as the binding site for the arginine repressor, argR.

The individual promoters of the artificial promoter libraries defined above are also comprised by the invention. Specific promoters which have been constructed according to the following examples are those stated in the SEQ IDs Nos. 5 to 58 below. The invention further comprises artificial promoters which are derived from promoters defined by the artificial promoter libraries of the invention.

The present invention also provides a method of constructing an artificial promoter library for a selected organism or group of organisms, which comprises selecting at least two consensus sequences of efficient promoters from said organism or group of organisms; synthesizing a mixture of single stranded DNA sequences comprising said consensus sequences, or parts thereof comprising at least half of each, and surrounding or intermediate nucleotide sequences (spacers) of variable length in which at least 7 nucleotides are selected randomly among the nucleobases A, T, C and G; and converting the single stranded DNA sequences into double stranded DNA fragments by second strand synthesis.

As previously mentioned, the broadest variation is obtained when at least 10, preferably at least 12, and more preferably at least 14, nucleotides in the spacer sequence(s) are selected randomly among the nucleobases A, T, C and G.

In order to obtain an artificial promoter library which is susceptible to regulation, the single stranded DNA sequences which are synthesized may include a regulatory DNA sequence imparting a specific regulatory feature to the promoters of the library. Such specific regulatory feature is preferably activation by a change in the growth conditions, such as a change in the pH, osmolarity, temperature or growth phase.

Also, in order to obtain an artificial promoter library suitable for cloning, a sequence specifying one or more recognition sites for restriction endonucleases may be added to one of or both the ends of the single stranded DNA sequences in the synthesis, or a linker comprising such restriction sites may be ligated to one of or both the ends of the double stranded DNA fragments. Most conveniently such sequences specify multiple recognition sites for restriction endonucleases (multiple cloning sites MCS).

The selected organisms for which artificial promoter libraries can be prepared by the method according to the invention and the various degenerated sequences to be chosen for the promoter libraries of specific organisms are the same as discussed above for the artificial promoter libraries per se.

With respect to possible uses of the artificial promoter libraries described above, the invention further provides a method of optimizing the expression of a gene in a microorganism, which comprises a) selecting a set of promoters covering a range of promoter activities in relatively small steps of activity change from an artificial promoter library b) cloning said set of promoters into said organism placing in each clone said gene under the control of at least one promoter from the set;

c) growing the selected clones and screening them to find the one showing optimized flux of product formation.

This method is preferably used with organisms selected from the group consisting of prokaryotic and eukaryotic microorganisms such as bacteria, yeasts, other fungi and mammalian cell lines.

In other aspects, the invention pertains to a method of isolating a promoter sequence being capable of optimizing the expression of a gene in a selected organism, the method comprising (i) constructing, using the above method of constructing a promoter library, a set of promoters covering, with respect to promoter strength, a range of promoter activities, (ii) cloning said set of promoters into the selected organism placing in each clone the gene to be expressed under the control of at least one promoter of the set, (iii) cultivating the clones and selecting the clone showing optimized flux of gene product formation, and (iv) isolating said promoter sequence from the clone showing optimized flux of gene product formation, and a promoter sequence that is capable of optimising the expression of a gene in a selected organism, which promoter sequence is obtainable by the above method of isolating a promoter sequence.

DETAILED DESCRIPTION OF THE INVENTION

Figure 1:
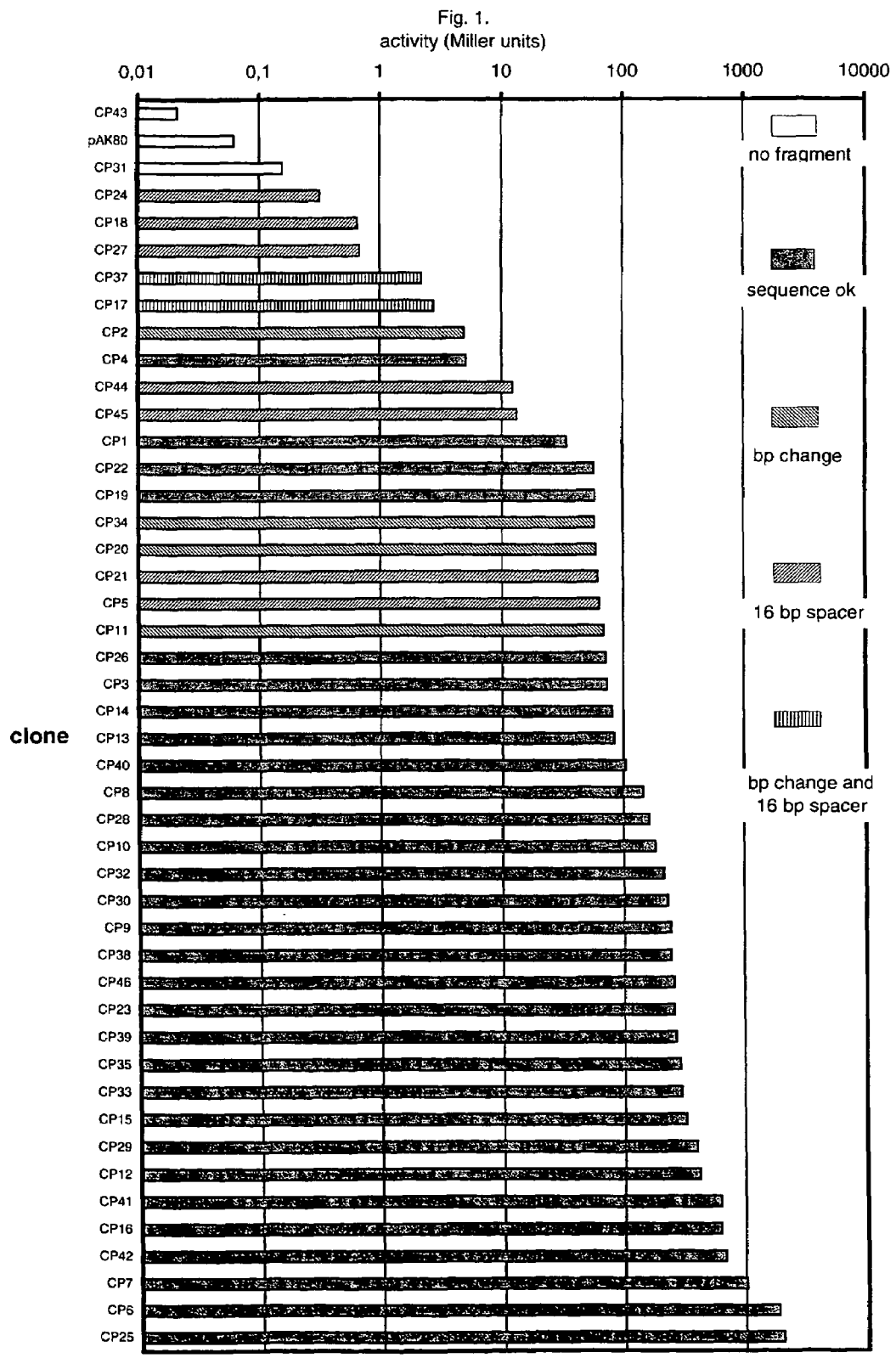
FIG. 1. A library of artificial promoters for *L. lactis*, from example 1. The promoter activities (Miller units) were assayed from the expression of a reporter gene (lacLM) encoding b-galactosidase transcribed from the different synthetic promoter clones, on the promoter cloning vector pAK80, in strain MG1363, grown in GM17 medium supplemented with 2 µg/ml erythromycin. The patterns of the data points indicate which promoter clones differed in either the −35 or the −10 consensus sequence, or in the length of the spacer between these two consensus sequences.

In our method, degenerated oligonucleotides are synthesized for the organism or group of organisms for which a promoter library should be constructed. The sequences of the oligonucleotides are written by combining the available knowledge from the literature, on the features that makes a promoter function efficiently in that particular organism. The amount of information that needs to be fixed in the oligonucleotide is somewhat variable among different organisms. In E. coli for instance, promoters of considerable strength may be formed by less perfect matches in the –35 and –10 consensus sequences and by spacing between these sequences deviating from 17 bp (TTGACA and TATAAT respectively), whereas the requirements for strong promoters in L. lactis appear to be more strict.

Secondly, the single stranded oligonucleotides are converted into double stranded DNA fragments and cloned into a promoter probing vector. The promoter-containing clones are identified e.g. by their ability to give colonies with various extents of colour on indicator plates. This should in principle give us only very strong promoters, but we discovered that by allowing the spacer sequences between the consensus sequences to vary in a random manner, the strength of the resulting promoters are modulated. In fact, using this method we obtained promoter libraries, spanning the entire range of promoter activities that is likely to become of interest, in small steps of activity change.

Optimization of gene expression could then be achieved as follows: 1) From the promoter library one chooses promoters that have e.g. 25%, 50%, 100%, 200% and 400% of the strength of the wild-type promoter. 2) Then, these promoters are cloned in place of the wild-type promoter upstream of the gene of interest. 3) The magnitude of the variable to be optimized (e.g. the flux through a pathway) that is obtained with each of these five constructs is then measured and the optimal construct is used directly as the production organism. It may be necessary to fine-tune the expression further or to expand the range of promoter activities. A direct advantage of this system over the inducible systems described above is that once the optimal promoter activity has been determined, the strain is in principle ready for use in the fermentation process.

In one preferred embodiment the random spacers method of the invention is used for generating a series of constitutive promoters for the Gram-positive bacterium, Lactococcus lactis. In other preferred embodiments we show that promoters generated by the random spacers method of the invention are functional in at least two species of Gram-negative bacteria, Escherichia coli and Pseudomonas, as well as in the Gram-positive bacterium Bacillus subtilis. We also show that the strength of the individual promoter is dependent on which organism it is being used in, i.e. that in some organisms a particular promoter is strong, in others it is weak, but in all the organisms tested, the promoters cover a broad range of activities, in small steps of activity change.

Often it is desirable to activate gene expression to a certain extent and at a certain stage of a fermentation, e.g. because the gene product that is expressed inhibits the growth of the cells. It is then useful to combine the above technique for obtaining promoters of different strength with some regulatory mechanism, e.g. so that the promoter will be activated by a change in the pH, temperature or growth phase.

Thus, in another preferred embodiment the random spacers method of the invention is used for generating a series of specifically regulated promoters. As illustrated in Example 2, the above approach is used in combination with specific regulatory DNA sequences to generate a library of heat-shock-regulated promoters for the Gram-positive bacterium, Lactococcus lactis.

In addition to prokaryotes, eukaryotic microorganisms (yeast and other fungi as well as mammalian cell lines,) are important microorganisms for production of a range of organic compounds and various proteins. It is therefore of interest to develop the above approach for modulating gene expression in these organisms as well. Thus, in yet another preferred embodiment, as illustrated in Example 7, the random spacers method of the invention is used for generating a series of promoters for the bakers yeast, Saccharomyces cerevisiae. The promoters are here equipped with GCN4p and ARGR regulation.

The regulation of transcription initiation in the eukaryotic cell is somewhat more complex compared to the prokaryote. The transcription start site is normally preceded by a so-called TATA box that contains the consensus sequence TATAAA or parts hereof, but unlike in the prokaryote, the distance from the TATA box to the transcription start site is much less defined. In Saccharomyces cerevisiae this distance is typically 40–120 nucleotides (Oliver and Warmington, 1989). The so-called –35 consensus hexamer which is found in many prokaryotic promoters is absent in Saccharomyces cerevisiae. Instead so-called upstream activation sequences (UAS) are found upstream of the transcription initiation site. These UAS are recognised by specific DNA binding proteins that can then act as activators of transcription initiation. For instance, the UAS sequence that is found upstream of the genes involved in aminoacid biosynthesis, $UAS_{GCN4p}$, consists of a DNA sequence that specifies a binding site for the GCN4 protein, which activates the transcription of these genes (Hinnebusch, 1992). In contrast to prokaryotes, where the distance between the promoter elements appears to be critical for the strength of promoters (see example 1), the distance between the TATA box and the UAS sequence in eukaryotic promoters is highly variable and may be up to about 1000 bp. Some genes even contain more than one copy of the UAS, but one seems to be sufficient for activation.

One of the UAS sequences known from yeast is the binding site for the GCN4 protein. Promoters that contain the binding site for GCN4 protein should be regulated by the status of amino acid supply in the growth medium: in the absence of amino acids, the GCN4 protein is formed and binds specific UAS sequences to stimulate transcription at promoters involved in biosynthesis of aminoacids. The consensus sequence for the GCN4 protein binding site ($UAS_{GCN4p}$) is a short inverted repeat, TGACTCA.

A promoter in Saccharomyces cerevisiae that is activated by the GCN4 protein is the ARG8 promoter. In this promoter, there is only one copy of the $UAS_{GCN4p}$ sequence, and it is located 59 bp from the TATA box (we refer to this distance as spacer 1). Transcription initiation takes place some 40–60 nucleotides downstream of the TATA box. The ARG8 promoter also contains a DNA sequence that functions as the binding site for the arginine repressor, argR (Crabeel et al., 1995), which makes the promoter four fold repressible by external arginine.

Thus, in this case the promoter is located within 136 bp, and it contains two regulatory features, which makes the system attractive for developing a promoter library by the random spacers method of the invention as outlined in the previous examples. But the method is not limited to this model system; in principle, any combinations of TATA boxes, UAS sequences, repressor binding sites etc., separated by spacers smaller than about 1000 nucleotides, should be suitable as a starting point for this method.

EXAMPLE 1

Design of a Degenerated Oligonucleotide for a *L. Lactis* Promoter Library.

According to the literature (see review in de Vos & Simons, 1994), strong promoters in *L. lactis* tend to have the following nucleotide sequences in common (numbers refer to the position relative to the transcription initiation site, which is given number +1): −12 to −7: TATAAT; −15 to −14: TG; −35 to −30: TTGACA. The spacing between −10 and −35 seems to be 17 nucleotides. However, closer comparison of the promoter sequences that have been published for *L. lactis* reveals that in a number of positions besides the ones mentioned above, nucleotides are more or less well conserved. Some of these positions are: −1: A; −3: A or T (=W); −6: A; −13: A or G (=R); −40 to −36: TATTC. In addition, Nilsson and Johansen (1994, BBA) pointed out two motives, +1 to +8: GTACTGTT, and −44 to −41: AGTT, that appear to be well conserved between relatively strong promoters (promoters for transfer RNA and ribosomal RNA operons) from *L. lactis*. These motives may confer both strength and growth rate dependent expression from the promoter.

When these additional motives are included, one arrives at the following 53 nucleobase degenerated sequence for an efficient promoter in *L. lactis*. Out of these 53 nucleobases, 34 bases are conserved two are semi-conserved (R and W) and 17 are allowed to vary randomly between the four nucleobases, SEQ ID NO:60:

5' AGTTTATTCTTGACANNNNNNNNNNNNNNNTGR TATAATANNWNAGTACTGTT 3'

In addition, this degenerated sequence is flanked by sequences that specify multiple recognition sites for restriction endonucleases (multiple cloning site MCS), and the actual oligonucleotide mixture to be synthesized has the following degenerated sequence reported in SEQ ID No. 1:

mentary to the 3' end of the promoter oligonucleotide. This oligonucleotide was then used as a primer for second strand synthesis by the Klenow fragment of DNA polymerase I in the presence of dATP, dCTP, dGTP and dTTP. In this way the second DNA strand became exactly complementary to the first DNA strand.

The result is a mixture of 100 bp double stranded DNA fragments containing multiple recognition sites for restriction endonucleases in both the 3' and 5' end. These DNA fragments were then cut with restriction endonucleases in order to create suitable "sticky" ends compatible with the ends of the vector DNA fragment, pAK80 (Israelsen et al., 1995). pAK80 is a shuttle vector, meaning that it has replication origins for propagation in both *E. coli* and *L. lactis*. In this way, the cloning steps can be conveniently performed in *E. coli*, while the subsequent physiological experiments can be done in *L. lactis*. Furthermore, pAK80 carries a promoterless β-galactosidase reporter gene system (lacLM) downstream a multiple cloning site. Thus, pAK80 does not express the lacLM genes, unless a promoter is inserted in the multiple cloning site.

Two cloning strategies were used for cloning the mixture of double stranded DNA fragments into the cloning vector pAK80:

1) The mixture was digested with BamHI and PstI and the vector pAK80 with PstI and BglII (BglII is compatible with BamHI).

2) The mixture was digested with SspI and HincII and the vector PAK80 with SmaI (all three enzymes produce blunt end DNA fragments).

In both cases the vector DNA was further treated with Calf Intestine Phosphatase (CIP) to prevent religation of the cloning vector. Subsequently, the fragment mixture and vector DNA were ligated overnight at 16° C. using T4 DNA ligase and standard ligation conditions.

Ligation mixtures were transformed into *E. coli* K-12 Δlac, with selection for erythromycin resistance. Cells of the *E. coli* K-12 strain, MT102, were made competent using standard treatment with Ca++ ions (Maniatis et al., 1982).

```
      MboI
      DpnI
      AlwI
      NlaIV
      BstYI
      BamHI MseI
      AlwI AflII SspI NsiI
  1      .      .        .          .          .          .          .
5'CGGGATCCTTAAGAATATTATGCATNNNNNAGTTTATTCTTGACANNNNNNNNNNNNNNNT

Alu I
                      Pvu II
                      NspBII
                   SfcI
               MseI  Fnu4HI
         RsaI  HpaI  PstI
         ScaI  HincII BbvI    EcoRI
61            .       .        .           100
 GRTATAATANNWNAGTACTGTTAACTGCAGCTGAATTCGG 3'
```

A mixture of oligonucleotides according to this specification was synthesized by Hobolth DNA synthesis.

This oligonucleotide mixture is single stranded initially and must be converted into double stranded DNA fragments for the purpose of cloning. This was done by synthesizing in vitro a 10 bp oligonucleotide, having a sequence comple- Ligation mixtures were then transformed into these cells using a standard transformation procedure (Maniatis et al., 1982), and the resulting clones were screened for β-galactosidase activity that will produce blue colonies on plates containing X-gal (5-bromo-4-chloro-3-indolyl-β-D-galactoside). The transformation mixture was plated on LB plates containing 200 µg/ml erythromycin, 1% glycerol and 100 µg/ml X-gal. 150 erythromycin resistant transformants were obtained, all white initially, but after prolonged incubation (two weeks at 4° C.), 46 of these colonies had become light blue. Thus, using strategy 1) we found 17 blue colonies (CP30 to CP46), and using strategy 2) we found 29 blue colonies (CP1 to CP29).

Plasmid DNA was isolated from each of these clones (CP1 to CP46) and analysed by restriction enzyme mapping. Nearly all plasmids (except CP31 and CP43) contained promoter fragments inserted into the MCS of pAK80, in the orientation that would direct transcription of the otherwise promoterless lacLM genes on this vector.

These 46 plasmid DNA preparations were then transformed into L. lactis subspecies lactis MG1363 with selection for erythromycin resistance. Cells of the L. lactis subspecies lactis strain, MG1363 (Gasson, 1983) were made competent by growing the cells overnight in SGM17 medium, containing 2% glycine, as described by Holo and Nes (1989). Plasmid DNA from each of the 46 clones described above was then transformed into these cells using the electroporation procedure (Holo and Nes, 1989). After regeneration, the cells were plated on SR plates containing 2 µg/ml erythromycin. Subsequent screening for blue color on X-gal plates revealed large differences in β-galactosidase activity between the 46 clones; some clones gave dark blue colonies after 24 hours of incubation, others only light blue colonies after more than 1 week of incubation.

The β-galactosidase activities of liquid cultures of the 46 clones in MG1363 were then determined as described by Miller (1972) and modified by Israelsen et al. (1995). Cultures of the strain MG1363, each carrying one of the 46 plasmid derivatives of pAK80, were grown in M17 medium supplemented with 1% glucose overnight at 30° C. 25–100 µl of these cultures were then used in the subsequent β-galactosidase assay, except in the case of the weakest promoter clones, where 2 ml of culture was used (after 20 fold concentration by centrifugation). These results are shown in FIG. 1. Apparently, there are very large differences in the efficiency of the cloned promoter fragments, and together these clones cover a range of promoter activities from 0.3 units of β-galactosidase activity to more than 2000 units, which is probably the strongest promoters known for this organism In addition, the broad range is covered by small changes in activity and, therefore, these promoter fragments will allow us not only to obtain a wide range of expression of genes in L. lactis, but also to tune the expression of genes in L. lactis in small steps for the purpose of flux optimization.

DNA sequencing of the 46 clones described above revealed that most of the inserted promoter fragments had the DNA sequence that was originally specified for the oligonucleotide design (see above), whereas the sequence of the remaining fragments deviated slightly from that sequence.

Most of the promoter fragments that gave the lower activities in the β-galactosidase assay (70 units of β-galactosidase or less) had either an error in one of the consensus sequences or a 16 bp spacer between the consensus sequences. This result is in accordance with the dogma, i.e. that changes in the consensus sequences have strong effects on the activity of a given promoter, and emphasizes the fact that a more subtle approach is needed in order to generate a promoter library that covers a range of activities in small steps of activity change. Clearly, if we would have allowed only changes in the consensus sequences and/or changes in the length of the spacer, instead of allowing the sequence of the spacers to vary randomly, only fairly weak promoter clones would have resulted, and the resulting library would not be suitable for metabolic engineering.

In general, the clones that gave high activities (more than 70 units) had the same sequence as specified by the oligonucleotide. In total, the activity of the clones that had intact consensus sequences and 17 basepair spacer length, spanned activities from 5 units (CP4) to 2000 units (CP25). These results therefore show that at least a 400 fold change in promoter activity can be obtained by randomizing the spacer while the consensus sequences are kept constant.

Usually, for metabolic engineering purposes, relatively strong promoters are desired. However, there may also be cases where rather weak promoters are needed. The relatively few errors that had occurred during synthesis of the above oligonucleotide mixture, were not intended to be present in the promoter fragments; and our data then suggest that it may be useful to generate, deliberately, a mixture of oligonucleotides which have a low percentage of errors in the consensus sequences.

Enzymes used in the various enzymatic reactions above were obtained from and used as recommended by Pharmacia and Boehringer.

EXAMPLE 2

Design of a Degenerated Oligonucleotide for a Library of Temperature Regulated in L. lactis Promoters.

This example illustrates the development of a temperature regulated promoter library for L. lactis. A regulatory element comprising an eight basepair inverted repeat that has been shown to be involved in the heatshock response of L. lactis is inserted a few base pairs upstream of the −35 sequence. The minimal extent of such a regulatory element seems to be 27 basepairs, SEQ ID NO:61:

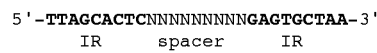
```
5'-TTAGCACTCNNNNNNNNNNGAGTGCTAA-3'
     IR       spacer      IR
``` containing a 9 bp (or longer) inverted repeat (IR) separated by 9 (or fewer) basepairs. It should therefore be possible to combine this inverted repeat with the approach for obtaining constitutive promoters of different strength and thus obtain a series of promoters with various basal activities which can be induced several fold by changing the temperature of the culture medium.

Therefore, an oligonucleotide was designed, which includes the core part (from position −35 to +6) of the sequence from the constitutive promoter series above (see example 1 and SEQ ID No. 1). The sequence upstream of the −35 hexamer has been replaced by the above inverted repeat sequence, and the sequence downstream of position +6 has also been modified, eliminating two conserved regions compared to example 1 (+1 to +8: GTACTGTT and −44 to −41: AGTT, which have been implicated in growth rate regulation, but which turned out to be dispensable with respect to creating strong promoters for L. lactis, see example 1). The sequence of the spacer (sp.1) between the two inverted DNA sequences in the inverted repeat was here allowed to vary randomly in order to see whether this had any effect on the temperature regulation of the resulting promoters, e.g. how many fold they could be induced by changing the temperature. The importance of the spacing (sp.2) between the inverted repeat and the −35 hexamer is not known, but in principle this region may contribute to or modulate the heatshock response of promoters. In order to limit the number of parameters, however, we have chosen here to include a naturally occurring configuration (derived from the dnaJ promoter from *L. lactis*; van Asseldonk et al., 1993): a short spacer sequence consisting of 5 times T.

When these sequences are combined, one arrives at the following 73 bp consensus sequence for a temperature regulated promoter in *L. lactis*. Out of these 73 bp, 45 are conserved, two are semi-conserved (R and W) and 26 are allowed to vary randomly between the four nucleobases, SEQ ID NO:62:

```
5'TTAGCACTCNNNNNNNNNNGAGTGCTAATTTTTTTGACANNNNNNNNNNN
    IR      spacer 1    IR     sp.2              spacer 3
NNNNTGRTATAATANNWNAGTACTG 3'
```

In addition, this degenerated sequence was flanked by sequences that specify multiple recognition sites for restriction endonucleases (multiple cloning sites MCS), and the actual oligonucleotide mixture that is being synthesized has the following degenerated sequence reported in SEQ ID No. 2:

```
    MboI
    DpnI
    AlwI
    NlaIV
    BstYI      MseI  MseI
    BamHI  AluI SspI
    AlwI  HindIII AseI
  1       .       .       .       .       .       .
5'CGGGATCCAAGCTTAATATTAATTAGCACTCNNNNNNNNNNGAGTGCTAATTTTTTTGACA
                              IR               IR         -35

Alu I
                              PvuII
                              NspBII
                         SfcI           EcoRI
                         PstI           ApoI
                    RsaI Fnu4HI  MaeI
                    ScaI BbvI    XbaI
61          .    A   .    T   .            .            . 113
NNNNNNNNNNNNNNNNTGGTATAATANNANAGTACTGCAGCTGTCTAGAATTCGG 3'
             -15   -10        +1
```

This oligonucleotide mixture was converted into double stranded DNA fragments (DSDF) and cloned into the promoter cloning vector pLB85i. pLB85i has an origin for replication in *E. coli* but not in *L. lactis* and selectable markers for both organisms. Instead of an origin of replication for *L. lactis*, it contains the attP sequence which can direct the insertion of the plasmid into the *L. lactis* chromosome if the int gene product is supplied in trans. This example therefore also serves to illustrate the modulation of chromosomally encoded genes, using promoters generated through the random spacers method. pLB85i is also a promoter cloning vector and contains a multiple cloning site upstream of a promoterless gusA gene. gusA is similar to the lacZ and lacLM screening systems used in the other examples, except that the substrate is X-gluc instead of X-gal. It was chosen as the reporter gene for this particular application, where heatshock regulated promoters are supposed to be analysed. This was because the gusA gene product is not heat labile, which seems to be a problem connected with the lacLM gene used in example 1.

Figure 2:
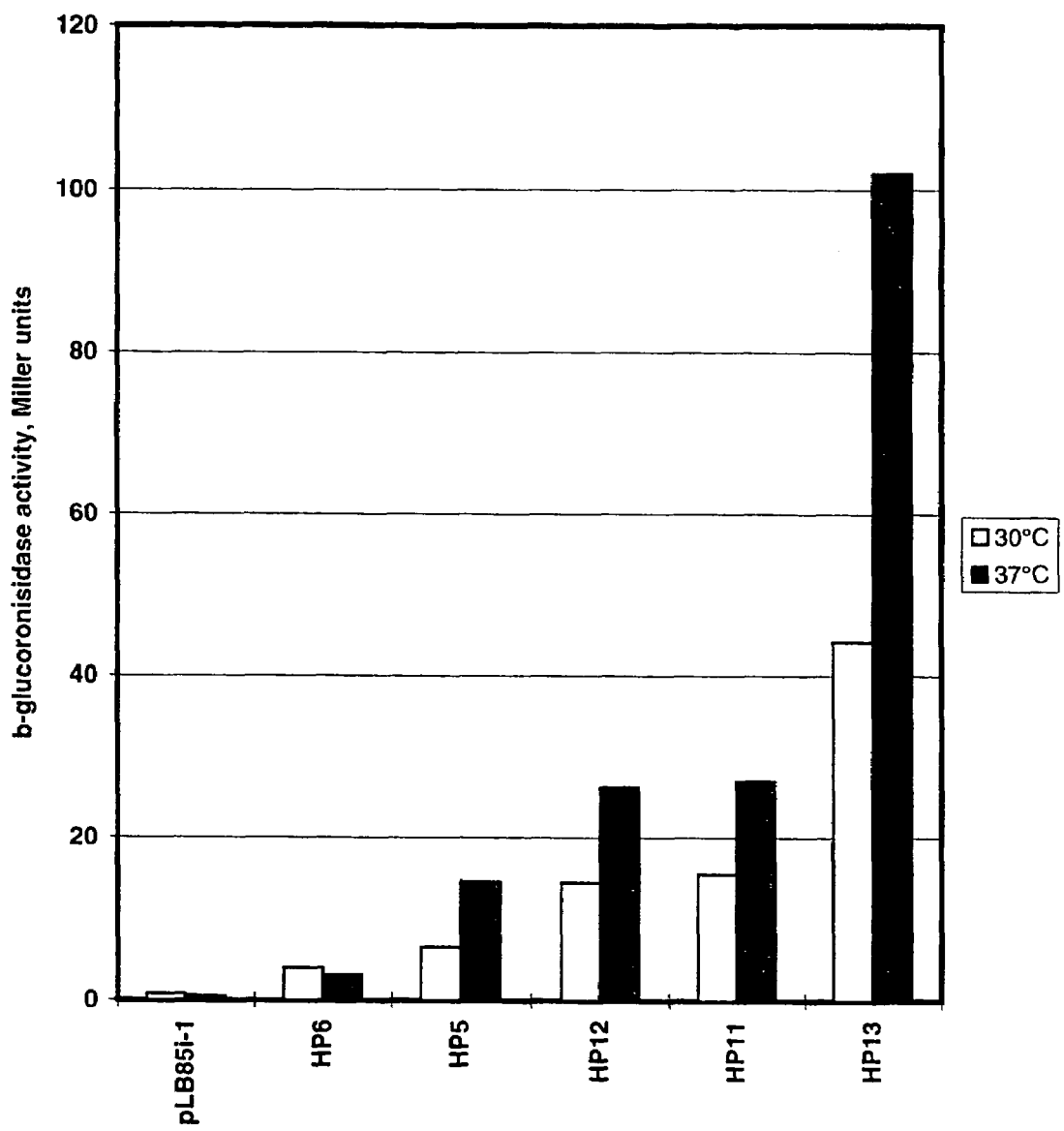
FIG. 2. A library of artificial heatshock regulated promoters for *L. lactis*, from example 2. The promoter activities (Miller units) were assayed from the expression of a reporter gene (gusA) encoding β-glucuronidase, transcribed from the different synthetic promoter clones, on the chromosome in strain LB436. The cells were grown in GM17 medium supplemented with 2 µg/ml erythromycin, and at two different temperatures, 30 and 37° C. The assay for β-glucuronidase was parallel to the β-galactosidase assay (see example 1) except that X-gluc was used as the substrate.

The DSDF mixture was here digested with XbaI and AseI and the vector pLB85i was digested with XbaI and NdeI (NdeI is compatible with AseI) and further treated with alkaline phosphatase to remove the 5 phosphate groups from the vector. After ligation of the DFDS mixture and the vector, the ligation mixture was transformed into strain KW1, a gusA negative *E. coli* strain, with selection for ampicillin resistance. This resulted in approximately 100 colonies of which 80% had different blue color intensities, indicating that these clones were carrying putative heatshock promoter fragments. 20 blue clones were picked for further analysis. Restriction analysis of plasmid preparations from these clones showed that they had inserts of approximately the right size. Subsequently, 6 of these plasmid preparations were used to transform LB436 (a derivative of *L. lactis* MG1363 which contain a second plasmid, pLB81, supplying the necessary int gene for integration of the plasmids into the attB site on the *L. lactis* chromosome). From each of the transformations colonies were isolated with putative integrations of the constructs into the attB attachment site on the *L. lactis* chromosome. The integration of the constructs was confirmed by standard colony PCR, using one primer in the attB region and one primer in the pLB85i region. The clones were subsequently tested for their ability to form blue colonies on GM17 medium supplemented with erythromycin and 100 µg/ml X-gluc at 30° C. and 37° C., respectively, and the clones showed a clear difference in color intensity at the two temperatures, indicating that the promoter activities were now under temperature regulation. Next the gusA expression from the heatshock promoters was measured in liquid cultures at the two temperatures, for 5 selected heatshock-regulated promoters, see FIG. 2. The clones had different activities and covered a broad range of promoter activities at 30° C., and 4 out of the 5 clones (all except HP6) gave higher promoter activities at 37° C., which shows that the promoters were indeed temperature regulated. Interestingly, the promoters were regulated by almost the same fold, i.e. from 1.7 to 2.3 fold by the temperature shift from 30 to 37° C., which indicates that the spacer (spacer 1) in the inverted repeat is of minor importance with respect to determining the fold of induction of these artificial promoters.

We have here been looking at the accumulated gusA activity, and although the data clearly show that the promoters are temperature regulated, one skilled in the art of analysing gene expression will appreciate that this makes it more difficult to observe the changes in promoter activities, that are brought about for instance by some change in external parameter such as temperature. In addition, it has been shown that the activity of heatshock regulated promoters is temporarily ten fold higher immediately after the temperature shift, than it appears when the steady state levels are compared as they are on FIG. 2. To observe the change in promoter activity more carefully, one should look at the rate of protein or mRNA synthesis, before and at various times after the perturbation in temperature. We therefore isolated RNA from the 5 clones at various times after the change in temperature from 30° C. to 37° C. and visualized the gusA mRNA by standard Nothern blotting (Maniatis et al., 1983), to analyze how many fold the individual promoter clone was induced by the temperature change.

EXAMPLE 3

The Gram-positive bacterium, *Bacillus subtilis* is used extensively as an industrial bioreactor for the production of a range of heterologous proteins. It was therefore of interest to test whether the random spacers method of the invention could also be used to generate promoter libraries for this organism. The consensus sequences for *Bacillus subtilis* are very similar to the consensus sequences for *E. coli* and *L. lactis*, and we could therefore test whether the approach was also valid for *Bacillus subtilis* by subcloning a number of CP promoters into a promoter cloning vector for this *Bacillus subtilis* and then ask 1) whether the CP promoters are active in *Bacillus subtilis* and 2) whether, also in this organism, the spacer between the consensus sequences plays an important role for the promoter strength. We chose to use the promoter cloning vector, pDG268, which is designed for integration of promoter fusions to lacZ into the amy locus on the *Bacillus subtilis* chromosome. The vector confers ampicillin and neomycin resistance, and it will replicate in *E. coli* for the initial cloning purposes, but not in *Bacillus subtilis*. When the linearized form of the vector is transformed into *Bacillus subtilis* it will be inserted into the amy locus on the *Bacillus subtilis* chromosome. This example therefore also serves as an example of the use of the promoters generated through the random spacers methods for modulation of chromosomally encoded genes.

The CP promoters were indeed active also in *Bacillus* subtilis, and the individual strength of the promoters were again very different from each other. The fact that the promoter library also covered a broad range of promoter activities in *Bacillus subtilis*, shows that the random spacers method is also valid for this organism.

EXAMPLE 4

Figure 3:
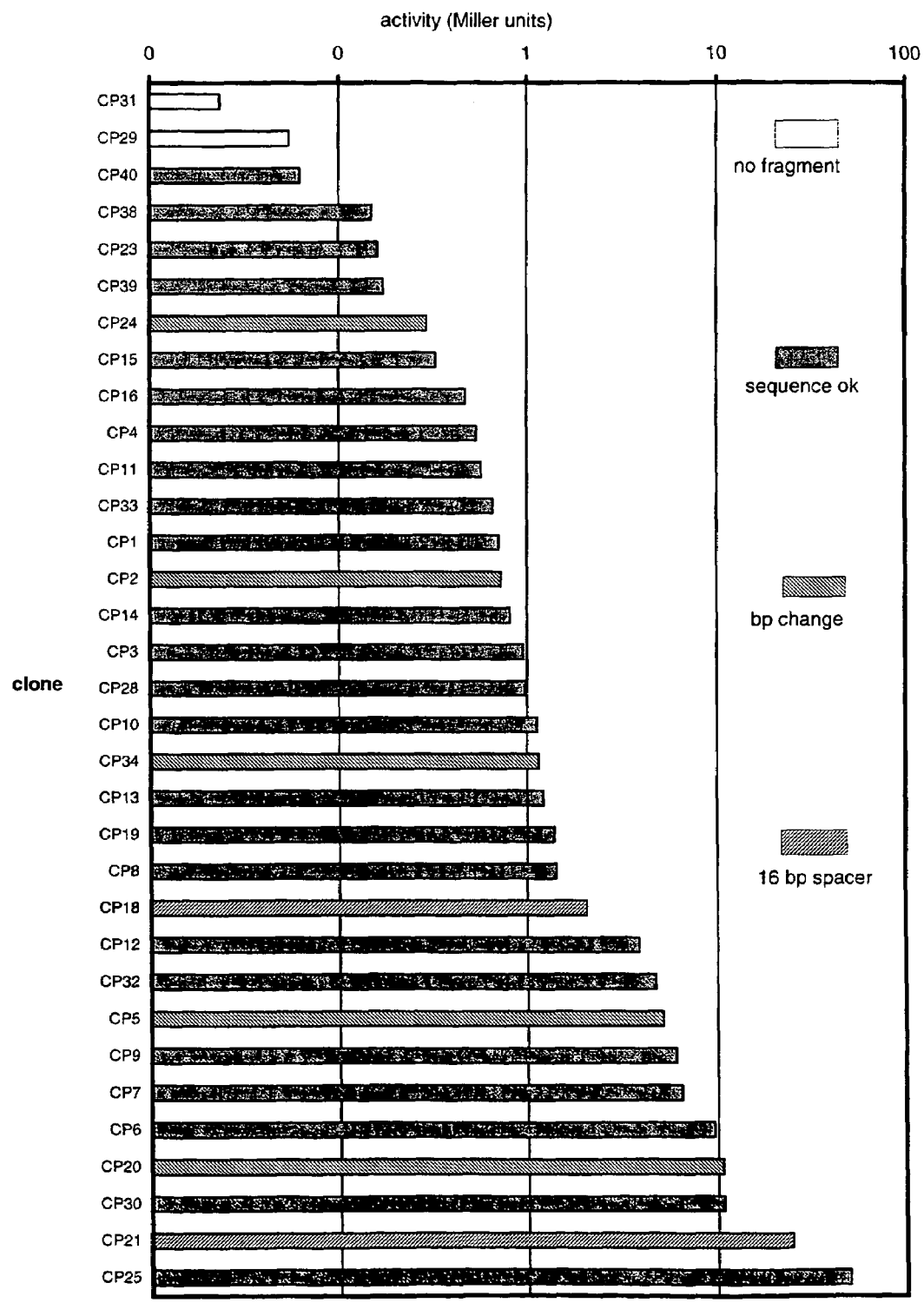
FIG. 3. The library of artificial promoters from example 1, assayed for activity in *E. coli*. The promoter activities (Miller units) were assayed from the expression of a reporter gene (lacLM) encoding β-galactosidase transcribed from the different synthetic promoter clones, on the promoter cloning vector pAK80, in strain BOE270, grown in LB medium supplemented with 200 µg/ml erythromycin. The patterns of the data points indicate which promoter clones differed in either the −35 or the −10 consensus sequence, or in the length of the spacer between these two consensus sequences.

The CP promoters of example 1 were designed for use in *L. lactis*, but the consensus sequences of *E. coli* promoters are included in the sequence of the oligonucleotide given in example 1. Furthermore, the vector used for generating the CP promoter library in example 1 is a shuttle vector for *L. lactis* and *E. coli*, so this also allowed us to analyse the activity of the CP promoters in the Gram-negative bacterial host, *E. coli*. FIG. 3 shows the activity of 33 of the CP promoters in *E. coli*. Clearly, the activity of the individual CP promoters is also here very different, and together the promoters cover a broad range of activities. Interestingly, the correlation between the strength of the individual promoters in *E. coli* and *L. lactis* was not very strong: some promoters that were found to be strong promoters in *L. lactis* were found to be weak in *E. coli* and vice versa.

The activity of the promoters, in terms of β-galactosidase activity, was generally much lower than the activity found in *L. lactis*. This was probably due to the fact that the promoter cloning vector, PAK80 is designed and optimised for use in the Gram-positive bacterium, *L. lactis*, and the translation efficiency in *E. coli* could therefore be low. We therefore sub-cloned three of the CP promoters (CP20, CP22 and CP25) into the promoter cloning vector, pCB267, which was designed for cloning *E. coli* promoters in upstream of a promoterless lacZ gene, encoding β-galactosidase. In this promoter system, the CP promoters turned out to be very efficient promoters, but the relative difference in strength between the three promoters was conserved. Thus, the CP25 promoter gave 2.5 fold higher activity than the hybrid promoter, ptac, which is considered to be among the strongest promoters known for use in *E. coli*. These data therefore further demonstrate the strength of our approach: by analysing a relatively small number of promoter clones obtained through the random spacers method of the invention, we have managed to arrive at some of the strongest promoters in both *E. coli* and *L. lactis*.

EXAMPLE 5

Bacteria belonging to the Gram-negative species, *Pseudomonas*, are becoming increasingly important due to their application in e.g. biodegradation of chemical waste products in polluted soil. But also here the genetic engineering is hampered by the lack of suitable promoters and expression systems. The literature on *Pseudomonas* promoters revealed that the consensus sequences for *Pseudomonas* are somewhat less well defined than those of *E. coli, L. lactis* and *Bacillus subtilis*. Thus, in the −35 region one often finds TTGR conserved (R=A or G) whereas the rest of the −35 consensus sequence is varying between different promoters. The −10 consensus sequence is probably TATRAT. The spacing between the TTGR motive and the −10 sequence is 18–19 bp, which is equivalent of the 16–17 bp spacer often found in *E. coli*. It follows that the consensus sequences for vegetative promoters in this organism are quite close to the consensus sequences for *E. coli* and *L. lactis*.

We therefore tested a range of the CP promoters from example 1 in *Pseudomonas putida* by cloning the promoters into a cloning vector that contains a promoterless β-galactosidase gene. Again the activity of the CP promoters differed in strength over a broad range of promoter activities. These results show that also in this species, the random spacers method of the invention could be used to generate both relatively strong promoters and also a broad range of promoter activities covered in small steps of activity change

EXAMPLE 6

We also designed an oligonucleotide based on the consensus sequences stated in example 5 and incorporated multiple cloning sites as described in example 1. The following oligonucleotide was synthesized (SEQ ID NO:4).

MCS-$(N)_8$-TTGR-$N_{19}$-TATRAT-$(N)_8$-MCS

The oligonucleotide was converted to double stranded DNA, using a primer homologous to the 3' end of the oligonucleotide and cloned upstream of a promoterless β-galactosidase gene on a promoter probe vector. The ligation mixture was transformed directly into a *Pseudomonas putida* strain with selection for the antibiotics resistance carried by the plasmid and on plates containing X-gal. This resulted in approximately 100 clones of various blue color intensities. Subsequently, 30 clones were analysed for β-galactosidase activity as described above. These results showed that also in this species, the random spacers method of the invention could be used to generate both relatively strong promoters and also a broad range of promoter activities covered in small steps of activity change.

EXAMPLE 7

Design of a Degenerated Oligonucleotide for a *Saccharomyces cerevisiae* Promoter Library.

A 199 bp oligonucleotide was designed, which includes, starting from the 5' end: an EcoRI restriction site (for use in the subsequent cloning strategy, see below), the consensus $UAS_{GCN4p}$, a 59 bp spacer (spacer 1), the consensus TATAAA sequence (TATA box), a 38 bp spacer (spacer 2), the 23 bp repressor binding sequence (which is also the region in which transcription is initiated), the spacer sequence between the TI box and the first codon of the ARG8 gene (this spacer is here the native sequence from the ARG8 gene including also the first codon of the ARG8 gene, ATG), and, finally, a BamHI site was included, which is designed to give an in frame fusion with the β-galactosidase reporter gene, see below.

Figure 4:
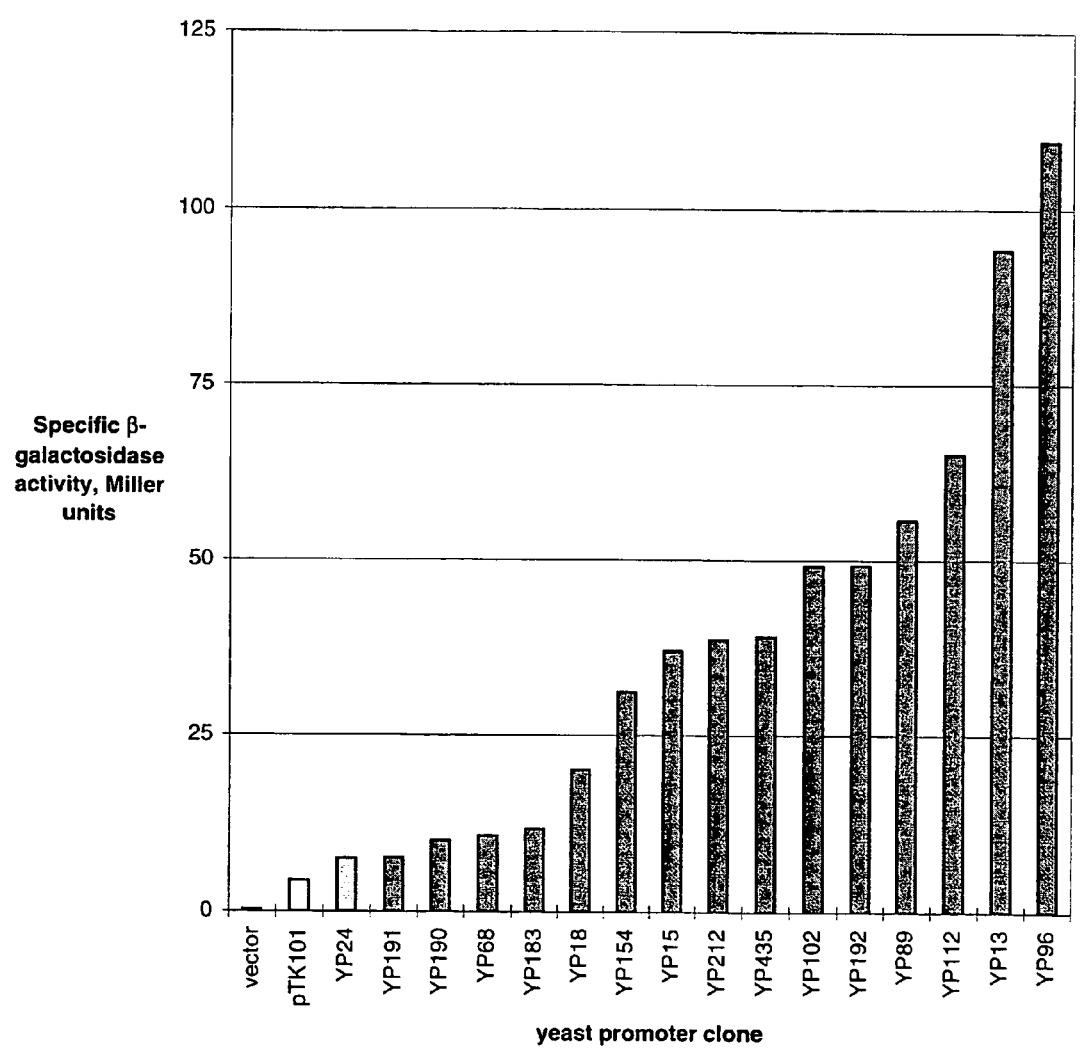
FIG. 4. A library of artificial promoters for *S. cerevisiae*, from example 7. The promoter activities (Miller units) were assayed from the expression of a reporter gene (lacZ) encoding β-galactosidase transcribed from the different synthetic promoter clones, on the promoter cloning vector pYLZ-2 in *S. cerevisiae* strain SG24 (URA3-52), grown in SD minimal medium supplemented with 2% glucose. YP24 and YP435 has a 1 bp deletion and a point mutation, respectively, in the $UAS_{GCN4p}$ binding site. pTK101 contains a promoter in which the UAS sequence has been deleted and the TATA box is present.

The sequences of spacer 1 and spacer 2 were allowed to vary randomly, and the actual oligonucleotide mixture being synthesized had the following degenerated sequence reported in SEQ ID No. 3:

17 clones were found to have an EcoRI-BamHI insert of approximately 200 bp. Plasmid DNA from these 17 clones were transformed into *S. cerevisiae*, with selection for the URA3 marker carried by the plasmids and assayed for production of β-galactosidase. FIG. 4 shows the resulting activities of β-galactosidase for the 17 clones. All the promoters have higher activities than the cloning vector itself without promoter fragment inserted (pYLZ-2). More important however, also in this case the clones cover a range of promoter activities in small steps of activity change.

Sequence analysis revealed that the 17 clones discussed above had a perfect TATA box (TATAAA) between the spacer 1 and spacer 2, while two of the 17 clones, YP24 and YP435 each had a defect in the $UAS_{GCN4p}$. However, the activity of YP435 was 39 units which is close to the value obtained with YP212. These data then suggest that the impact of the random sequence of the spacers on the promoter strength, is stronger than the impact of the state of the $UAS_{GCN4p}$ binding site.

As discussed above, the artificial yeast promoters had built in two different regulatory features. One is that the promoters should be regulated by the presence of arginine in the growth medium. To test whether the artificial yeast promoters were also regulated by arginine, we grew a number of clones in minimal medium, with and without

Figure 5:
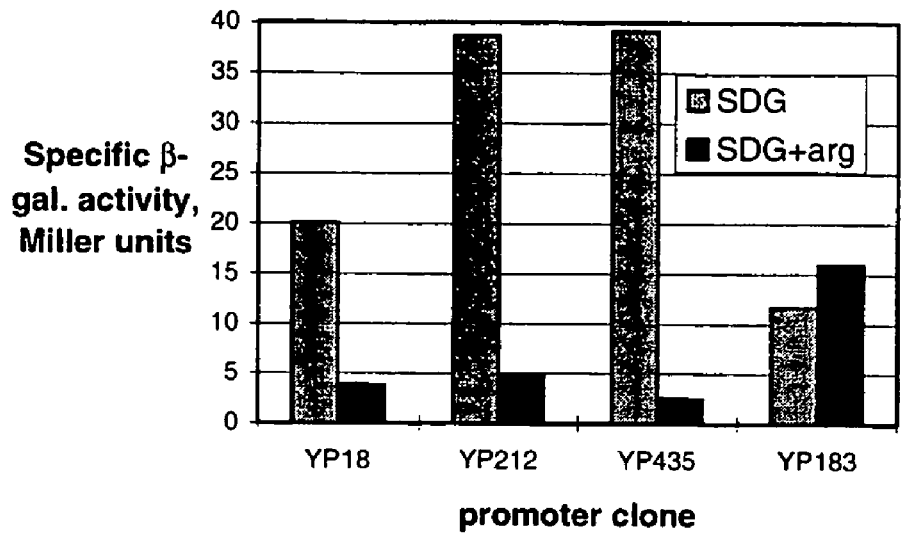
FIG. 5. Regulation of artificial yeast promoters by external arginine, from example 7. The promoter activities (Miller units) were assayed from the expression of a reporter gene (lacZ) encoding β-galactosidase transcribed from the different synthetic promoter clones, on the promoter cloning vector pYLZ-2 in *S. cerevisiae* strain SG24 (URA3-52), grown in SD minimal medium supplemented with 2% glucose, with (SDG) or without 1 g/l arginine (SDG+arg). YP183 has a 13 bp deletion in the binding site for the argR repressor.

This oligonucleotide mixture was converted into double stranded DNA fragments (DSDF), using an oligonucleotide complementary to the last 23 bp of the 3' end of the 199 bp degenerated oligonucleotide as described in example 1. Subsequently, it was cloned into either of the two promoter cloning vectors, pYLZ-2 and pYLZ-6 (Hermann et al., 1992), as follows: the DSDF mixture and the vector were both double-digested with EcoRI and BamHI, and the DSDF were ligated to the vector DNA. The ligation mixture was transformed into *E. coli* as described in example 1, with selection for ampicillin resistance. Plasmid DNA was isolated from 500 individual clones and screened for the presence of putative promoter fragments by digestion with the restriction enzymes, EcoRI and BamHI.

arginine (SD+2% glucose; SD+2% glucose+1 g/l arginine). FIG. 5 shows the result of these experiments. The clones, YP18, YP212, YP435 were indeed regulated 5, 8, 15 fold, respectively, by the presence of arginine. YP183 was not regulated by arginine, and sequence analysis confirmed that this promoter clone had a 13 bp deletion in the arginine repressor binding site.

Figure 6:
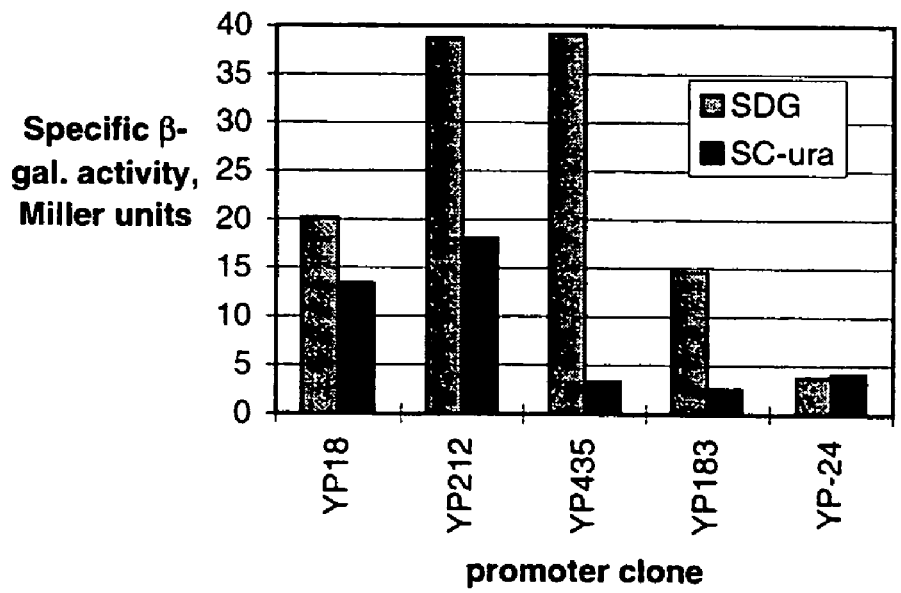
FIG. 6. Regulation of artificial yeast promoters by external amino acids, from example 7. The promoter activities (Miller units) were assayed from the expression of a reporter gene (lacZ) encoding β-galactosidase transcribed from the different synthetic promoter clones, on the promoter cloning vector pYLZ-2 in *S. cerevisiae* strain SG24 (URA3-52), grown in SD minimal medium supplemented with 2% glucose (SDG) or complex medium (containing amino acids) without uracil (sc-ura), YP24 has a 1 bp deletion in the $UAS_{GCN4p}$ binding site.

We also tested whether the promoters were regulated by external amino acids in the growth medium, by analyzing the promoter activity of some of the yeast promoter clones in minimal medium (SD+2% glucose) and rich medium (SC+2% glucose-URA). FIG. 6 shows the result of these experiments. Indeed, the promoters present in clones YP18, YP212, YP435, and YP183 were regulated from 2 to 10 fold, by the presence of amino acids. YP24 was not regulated, in accordance with the error that had occurred in the UAS$_{GCN4p}$ site on this clone, see above.

The results on amino acid and specific arginine regulation demonstrate that the random spacers method of the invention can be used for generating promoters which cover a broad range of promoter activities and which can be regulated by external signals. The regulatory aspect of the invention is here exemplified by the amino acid and arginine regulation, but is not limited to these cases.

REFERENCES

Crabeel, M., de Rijcke, M., Seneca, S., Heimberg, H., Pfeiffer, I., and Matisova, A., 1995. Further definition of the sequence and position requirements of the arginine control element that mediates repression and induction by arginine in *Saccharomyces cerevisiae. Yeast* 11: 1367–1380 de Vos, W. M., and Simons, G., 1994. Gene cloning and expression systems in lactococci, p. 52–105. In M. J. Gasson and W. M. de Vos (eds.), Genetics and biotechnology of lactic acid bacteria. Blackie Academic & Professional, Glasgow, United Kingdom.

Gasson, M. J. 1983. Plasmid complements of *Streptococcus lactis* NCDO 712 and other lactic streptococci after protoplast-induced curing. *J. Bacteriol.*, 154, 1–9.

Guarente, L., 1983. Yeast promoters and lacZ fusions designed to study expression of cloned genes in yeast. *Methods Enzymol.* 101, 181–191.

Hermann, H., Hacker, U., Bandlow, W., and Magdolen, V., 1992. pYLZ vectors: *Saccharomyces cerevisiae/Escherichia coli* shuttle plasmids to analyze yeast promoters. Gene 119: 137–41.

Hinnebusch, A. G., 1992. General and Pathway-specific Regulatory Mechanisms Controlling the Synthesis of Amino Acid Biosynthetic Enzymes in *Saccharomyces cerevisiae*, p. 319–414. In E. W. Jones, J. R. Pringle and J. R. Broach (eds.), The Molecular and Cellular Biology of the Yeast *Saccharomyces*: Gene Expression. Cold Spring Harbor Laboratory Press, Cold Spring Harbor, N.Y.

Holo, H., and Nes, I. F., 1989. High frequency transformation, by electroporation, of *Lactococcus lactis* subsp. *cremoris* grown with glycine in osmotically stabilized media. *Appl. Environ. Microbiol.*, 55, 3119–3123.

Israelsen, H. 1995. Cloning and partial characterization of regulated promoters from *Lactococcus lactis* Tn917-lacZ integrants with the new promoter probe vector, pAK80. *Appl. Environ. Microbiol.*, 61, 2540–2547.

Jensen, P. R., Westerhoff, H. V., and Michelsen, O., 1993. Excess capacity of H$^+$-ATPase and inverse respiratory control in *Escherichia coli. EMBO J.*, 12, 1277–1282.

Kacser, H. and Burns, J. A. 1973. The control of flux. *Symp. Soc. Exp. Biol.*, 27: 65–104.

Maniatis, T., Fritsch, E. F., and Sambrook, J., 1982. *Molecular cloning*. Cold Spring Harbor Laboratory Press, Cold Spring Harbor, N.Y.

Miller, J. H., 1972. *Experiments in molecular genetics*, Cold Spring Harbor Laboratory Press, Cold Spring Harbor, N.Y.

Nilsson, D., and Johansen, E., 1994. A conserved sequence in tRNA and rRNA promoters of *Lactococcus lactis. Biochim. Biophys. Acta*, 1219: 141–144.

Oliver, S. G., and Warmington, J. R., 1989. Transcription. In *The yeasts, volume* 3, Rose and Harrison (Eds.). Academic Press, London, 117–160.

Schaaff, I., Heinisch, J., Zimmermann, F. K., 1989. Overproduction of glycolytic enzymes in yeast. Yeast, 5: 285–290.

van Asseldonk, M., Simons, A., Visser, H., de Vos, W. M., and Simons, G., 1993. Cloning, nucleotide sequence, and regulatory analysis of the *Lactococcus lactis* dnaJ gene. *J. Bacteriol.* 175, 1637–1644.

The invention claimed is:

1. An isolated promoter sequence selected from the group consisting of SEQ ID NO:5, SEQ ID NO:6, SEQ ID NO:7, SEQ ID NO:8, SEQ ID NO:9, SEQ ID NO:10, SEQ ID NO: 11, SEQ ID NO: 12, SEQ ID NO: 13, SEQ ID NO: 14, SEQ ID NO: 15, SEQ ID NO: 16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, and SEQ ID NO:58.

* * * * *